United States Patent [19]

Christidis et al.

[11] 4,105,690
[45] Aug. 8, 1978

[54] PROCESS FOR MANUFACTURING N-ACYL DERIVATIVES OF HYDROXY-ARYLGLYCINES

[75] Inventors: Yani Christidis, Paris; Alain Schouteten, Villiers le Bel, both of France

[73] Assignee: Nobel Hoechst Chimie, Puteaux, France

[21] Appl. No.: 722,284

[22] Filed: Sep. 10, 1976

[30] Foreign Application Priority Data

Sep. 12, 1975 [FR] France .................... 75 28151
Jan. 16, 1976 [FR] France .................... 76 01178

[51] Int. Cl.² ............... C07C 102/00; C07C 103/30; C07C 103/46; C07C 103/66
[52] U.S. Cl. .................... 260/519; 260/343.3 R; 260/534 M
[58] Field of Search ........................ 260/519

[56] References Cited

U.S. PATENT DOCUMENTS 3,860,631  1/1975  Gleason .................... 260/519

Primary Examiner—Vivian Garner
Attorney, Agent, or Firm—Karl W. Flocks

[57] ABSTRACT

Condensation of the addition product of glyoxylic acid and amides with hydroxyaryl compounds is effected by a first step, wherein the reaction is carried out hot, at a temperature below 60° C, of an aliphatic amide having at the most 4 carbon atoms selected from the group of acetamide, chloracetamide, propionamide, acrylamide and butyramide, on an aqueous solution of glyoxylic acid. Then in a second step, after the addition of acetic acid and gaseous hydrochloric acid, condensation is effected at a temperature below 35° C of the carboxamidoglycolic acid with an excess reaching 500% of hydroxyaryl compound selected from the group comprising phenol and its alkyl derivatives, their halogen derivatives, polyphenols and their ethers and betanaphthol. After the condensation of said second step, the volatile products are removed by vacuum distillation. When the hydroxyaryl compound is phenol, the crude product resulting from this distillation is taken up in nitromethane or water, which are a non-solvent of the N-acyl derivative of parahydroxyphenylglycine but a solvent of the corresponding ortho derivative; the proportion of the para derivative in the resulting compound is then of the order of 100%.

7 Claims, No Drawings

PROCESS FOR MANUFACTURING N-ACYL DERIVATIVES OF HYDROXY-ARYLGLYCINES

BACKGROUND OF THE INVENTION

1. Field of the Invention

The present invention relates to the manufacture of N-acyl derivatives of hydroxyarylglycines and to novel products resulting therefrom.

2. Description of the Prior Art

The hydroxyarylglycines and particularly D-p-hydroxyphenylglycine are at present used in the manufacture of semi-synthetic penicillins. For this use, whether for the separation of enanthiomorphs or for reaction with penicillins, the —$NH_2$ group has to be protected by a group easily hydrolysable subsequently, for example an acyl group. The N-acyl derivatives of hydroxyarylglycines or N-2-acylamido-2-(hydroxyaryl) acetic acids hence constitute valuable intermediate products in the preparation of semi-synthetic penicillins. They are usually obtained by acylation of the corresponding hydroxyarylglycines, themselves prepared by the conventional methods of amino acid synthesis.

Among these methods, that of STRECKER and its modification, the method of BUCHERER, have been employed for a long time. They consist essentially of reacting an aldehyde, in the first case, with an alkali cyanide and ammonia, to obtain an α-aminoitrile, in the second case, with an alkali cyanide and ammonium carbonate to obtain a hydantoin, this nitrile or this hydantoin being then hydrolysed in an acid medium (ULLMANNS ENCYKLOPADIE DER TECHNISCHEN CHEMIE- Vol. 3, page 507). They have the drawback of being rather long and complicated and especially of using as a raw material, an aromatic aldehyde, which is an expensive substance.

A simpler method of synthesizing hydroxyarylglycines consists of condensing by a Mannich reaction, glyoxylic acid with a phenol and ammonia (French Pat. Nos. 71 25034 and 71 36918). The yields of this condensation are not very high and they are further reduced by the need to acylate the product obtained.

Recently, it has been proposed, to avoid the additional step constituted by protecting the -$NH_2$ group, to synthesize directly hydroxyarylglycines whose nitrogen is protected. A first process consists of reacting glyoxylic acid with phenol and a nitrogen compound such as a carbamate, a thiocarbamate, a urea derivative or an amide (French Pat. Application No. 74 38338) in which the nitrogen is already protected. However, this method, for which moreover only examples with carbamates are given, leads, with phenols whose ortho and para positions are free, to mixtures of derivatives including α-aminoacetic groups at the ortho and para positions with yields which, to applicants' knowledge, are apparently uninteresting from the industrial point of view.

A second process consists of preparing in a first phase in an organic solvent medium, an adduct product of glyoxylic acid with an aromatic amide (U. ZOLLER and D. BEN ISHAI — Tetrahedron — Vol. 31 — p. 863-866 (1975)) then of condensing this product with a hydroxyaryl compound in an acetic acid/sulfuric acid medium (D. BEN ISHAI, I. SATATI and Z. BERLER — J.C.S. Chem. Comm — No. 9 — 7/5/75 p. 349). The latter process, if it enables satisfactory yields to be obtained, has the drawback of using aromatic amides which are not manufactured industrially and of fixing an acyl residue which is uselessly heavy and expensive, since it is destined to disappear in the course of the subsequent yields of the N-acyl derivative. In addition, it applies glyoxylic acid in the form of the hydrate, a product which is expensive and which is not manufactured industrially either.

This process using sulfuric acid or a mixture of acetic acid/sulfuric acid as the reaction medium is not usable when an amide is used which is an aliphatic amide as a result of the solubility of the final product in the reaction medium and the difficulty of extracting it.

OBJECTS AND GENERAL DESCRIPTION OF THE INVENTION

It is an object of the present invention to overcome the abovementioned drawbacks.

It is another object of the invention to provide a process whereby there are obtained, from aliphatic amides, better yields and purer products than those obtained with the known process for aromatic amides and using sulfuric acid as a reaction medium.

It is a further object of the invention to provide a process which enables the introduction of an acyl group of low molecular weight and the use of industrially manufactured amides.

It is yet another object of the invention to provide a process which permits easy separation of the final product obtained and, in the case of the condensation with phenol itself, to obtain a mixture of ortho and para derivatives which contain a proportion of at least 70% of para derivative which can be increased up to about 100% by very simple subsequent processing.

It is a further object of the invention to provide a process which enables novel products to be obtained.

Other objects and advantages of the invention will become apparent from the description which follows.

According to the invention it has been found that it is possible by a process not having these drawbacks to obtain N-acyl derivatives of hydroxyarylglycines and principally of p-hydroxyphenylglycines with aliphatic acyl radicals by reacting in a first phase in aqueous medium aliphatic amides with glyoxylic acid, then by condensing in a second phase at low temperature, the carboxamidoglycolic acid obtained, as is or isolated by crystallisation, with a hydroxyaryl compound, in an acetic acid medium, in the presence of gaseous hydrochloric acid.

The sequence of reactions may be represented diagrammatically as follows in the case of the condensation of guaiacol:

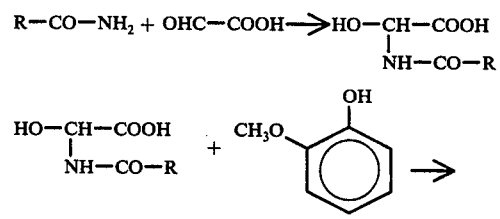

-continued

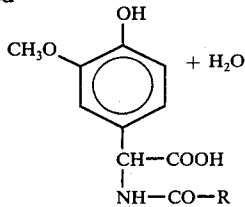

In the process according to the invention, in a first phase, an acylamido-glycolic acid is prepared of the formula

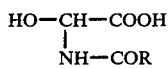

in which R is a saturated or unsaturated alkyl radical, possibly substituted, by the action with heating of the amide R—CONH$_2$ on the glyoxylic acid in aqueous solution, then eliminating the major portion of the water under vacuum; in a second phase, the product obtained, as is or isolated in the form of a hydrate, is supplemented with acetic acid and gaseous hydrochloric acid then condensed at low temperature with an excess of hydroxyaryl compound.

The final condensation product is isolated from the reaction medium by known processes, which can vary according to the properties and physical condition of this final product. It is possible for example to remove by distillation under vacuum the major portion of the acetic and hydrochloric acids and the water.

When the hydroxyaryl compound is phenol itself, there are obtained thus as has been indicated above, a mixture of derivatives substituted at the ortho and at the para positions containing at least 70% of the para derivative. By treating this mixture, without intermediate separation, if necessary hot, by means of a non-solvent of the para derivative, but solvent of the ortho derivative which may be present or its lactone, such as nitromethane or water, it is possible to obtain a product containing 100% of the para derivative.

Of course, it is possible from N-acyl derivatives of hydroxyarylglycines, to obtain easily the hydroxyarylglycines themselves by deacylation according to known methods, for example by boiling with an aqueous solution of hydrochloric acid.

The first phase of the process consisting of causing the amide R—CONH$_2$ to react with the glyoxylic acid is carried out preferably below 60° C. It is possible, if necessary after the removal of the major portion of water, to isolate the carboxamidoglycolic acid by crystallisation. The carboxamidoglycolic acid can also be prepared by the process described for acrylamidoglycolic acid in French Pat. No. 1 411 715 (namely by condensation in an aqueous medium at pH 7-9, of an alkali salt of glyoxylic acid with acrylamide then acidification to liberate the acid).

The second phase of the process relating to the condensation of the acylamidoglycolic acid with the hydroxyaryl compound is carried out preferably at a temperature below 35° C. The molecular excess of hydroxyaryl compound with respect to the glyoxylic acid and to the amide can reach 500%, and is a function of the reactivity of the hydroxyaryl compound.

The amides usable for the preparation of the carboxamidoglycolic acids are all amides of the formula R—CO—NH$_2$ in which R has the above-indicated significa-tion. It is particularly advantageous to use amides including at the most 4 carbon atoms. Among these amides, may be mentioned acetamide, chloroacetamide, propionamide, acrylamide and butyramide.

It goes without saying that when an unsaturated amide is used, its polymerisation in the course of the various reactions should be prevented by means of a suitable polymerisation inhibitor, for example a copper salt.

The hydroxyaryl compounds condensable with carboxamidoglycolic acids may be any compound including one or several aromatic nuclei and at least one hydroxyl group and possibly other substituents provided that they possess at least one free position at para or ortho, with respect to the hydroxyl group. It is self-evident that the condensation will occur more easily if this free position is not subject to steric hindrance due to the fact of the existance of bulky substituents in the neighbouring positions.

When the para and ortho positions with respect to the hydroxyl are free, the condensation with the carboxamidoglycolic acid is effected especially at the para position. When the para position is not free and the condensation is effected at the ortho position, the at least partial formation of a lactone can occur by the reaction of the phenolic hydroxyl with the carboxylic group.

As hydroxyaryl compounds, it is possible to use advantageously phenol and its alkyl derivatives (cresols, xylenols, 2,6-di-tertiary-butyl phenol), their halogen derivatives, polyphenols (pyrocatechol, resorcinol, hydroquinone, pyrogallol) and their ethers (guaiacol, gaethol, hydroquinone mono-methyl ether, 2,6-dimethoxy phenol), β-naphthol, etc.

Thus as has been mentioned above, the N-acyl derivatives of hydroxyarylglycines prepared according to the process of the invention are important intermediate products for the manufacture of semi-synthetic penicillins.

DESCRIPTION OF PREFERRED EMBODIMENTS

The following examples are given for the purpose of illustrating the invention but are not to be regarded as in any way limiting.

EXAMPLE 1

Acetamidoglycolic acid

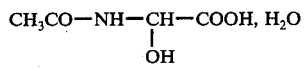

888 g of an aqueous solution with 50% of glyoxylic acid (6 moles) is mixed with 354 g of acetamide (6 moles). The mixture is kept at 50° C for 8 hours. By cooling slowly to 10° C, crystallisation occurs. The product separated is dried at low temperature on a fluidised bed. 415 g of dry product are obtained. By concentration of the mother liquors under vacuum, a further 123 g of product are recovered.

The yield is 54.5% of product having the following characteristics:
 MP = 57° C
 water = 13% (theory 11.9%)
 acidimetry = 99.5% of theory

| Elementary analysis | Calculated | Found |
|---|---|---|
| C | 31.8% | 31.8% |
| H | 5.95% | 5.7% |
| N | 9.25% | 9.2% |

EXAMPLE 2

Chloracetamidoglycolic acid

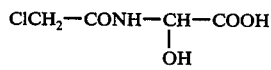

740 g of an aqueous solution with 50% of glyoxylic acid (5 moles) are mixed with 514 g of chloracetamide (5.5 moles). The mixture is heated to 50° C, then the greater part of the water is removed under vacuum, 1200 g of acetic acid are added and it is cooled on ice. After filtration and drying, 475 g of product are obtained. The product concentrated under vacuum gives 112 g of a second crop, namely a total yield of 69%.

1st crop MP = 105° C
Titration by acidimetry =99.3% of theory

| Elementary analysis | Calculated | Found |
|---|---|---|
| C | 28.7% | 28.7% |
| H | 3.6% | 3.6% |
| N | 8.36% | 8.4% |

EXAMPLE 3

Acrylamidoglycolic acid

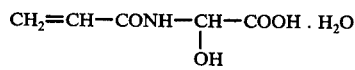

Heating is carried out at 40° C for 6 hours of a mixture of 888 g (6 moles) of an aqueous 50% glyoxylic acid solution, 426 g (6 moles) of acrylamide and 0.20 g of copper acetate. It is then cooled to 15° C, drained, washed with acetone and dried on a fluidised bed at 50° C.

430 g of crystallised product are obtained namely a yield of 44% with respect to the glyoxylic acid.

The mother liquors are used in a second operation under the same conditions as above, but with an aqueous 60% glyoxylic acid solution. The cumulated yield of this operation with the preceding one is 63% with respect to the glyoxylic acid. The reutilisation of the mother liquors enables after 10 operations, a cumulated yield to be obtained of 88% with respect to the glyoxylic acid, of a product titrating 99.5% by acidimetry and 98% by measurement of the double bonds and containing less than 5 ppm of $Cu^{++}$.

EXAMPLE 4

N-acetyl (4-hydroxy,3-methoxy phenyl)glycine

At 5° C a solution is made of 18.5 g of gaseous HCl in a solution of 68.3 g (0.55 mole) of guaiacol in 120 g of glacial acetic acid. After the addition of 75.5 g (0.5 mole) of acetamidoglycolic acid (hydrate) it is kept for 6 hours at 5° C then for 16 hours at 20° C. It is then poured into 600 ml of water. 110 g of dry product are obtained (yield 92%). The product recrystallised from water (yield 80%) has the following characteristics:

MP = 268° C
Acidimetry = 4.35 m eq/g (theory 4.18)

| Elementary analysis | Calculated | Found |
|---|---|---|
| C | 55.23% | 55.2% |
| H | 5.44% | 5.5% |
| N | 5.86% | 5.85% |

By deacetylation by heating to boiling for 7 hours under nitrogen with dilute HCl, the free amino acid is obtained (yield 90%).

MP = 225° C (with decomposition)

EXAMPLE 5

3,4-dihydroxy phenylglycine by means of the N-acetyl derivative

Under vacuum at 50° C there is concentrated a mixture of 29.5 g (0.5 mole) of acetamide, 74 g (0.5 mole) of 50% glyoxylic acid, then it is kept for 4 hours at 50° C after the addition of 120 g of glacial acetic acid. Following cooling to 20° C, 60.6 g (0.55 mole) of pyrocatechol are dissolved therein, then at 5° C, 18 g of gaseous HCl. After 6 hours at 5° C then 16 hours at 20° C, the acetic and hydrochloric acids are distilled off under vacuum at 60° C. 62 g of crude N-acetyl product are obtained which are deacetylated by boiling for 3 hours with 500 ml of water and 150 ml of concentrated HCl. After concentration, crystallisation is carried out at pH 6 and 71 g of the crude amino acid are obtained which, after recrystallisation in water, provide 55 g of purified product, namely a yield of 55% with respect to the glyoxylic acid.

MP = 186° C

| Elementary analysis | Calculated | Found |
|---|---|---|
| C | 47.8% | 47.7% |
| H | 5.5% | 5.5% |
| N | 7.0% | 7.0% |

EXAMPLE 6

2,3,4-trihydroxy phenyl glycine by means of its acetyl derivative

To a solution of 19 g of HCl and 69.5 g (0.55 mole) of pyrogallol in 240 g of glacial acetic acid, are added at 10° C, 75.5 g (0.5 mole) of acetamidoglycolic acid (hydrate). After 6 hours at 10° C under nitrogen, 360 g of acetic acid are added and it is kept for 15 hours at room temperature, then distilled at 50° C under 20 mm of mercury. The residue is suspended in 300 ml of nitromethane, then separated and dried (yield 88%).

24.1 g of the crude product deacetylated by heating with dilute HCl gives 14.3 g of 2,3,4-trihydroxy phenyl glycine containing 11.8% of water.

MP = 200° C (with decomposition)

| Elementary analysis (taking the water into account) | Calculated | Found |
|---|---|---|
| C | 48.24% | 48.1% |
| N | 7.04% | 7.7% |

EXAMPLE 7

N-acetyl (4-hydroxy phenyl) glycine

An acetic acid solution of acetamidoglycolic acid is prepared by distilling under vacuum without exceeding 40° C the water from a mixture of 74 g of aqueous solution of 50% glyoxylic acid (0.5 mole) and 29.55 g of acetamide (0.5 mole).

After distillation of 28 g of water, 120 g of glacial acetic acid are added and it is kept for 3 hours at 40° C. After the addition of 188 g (2 moles) of phenol, 63 g of gaseous HCl are absorbed without exceeding 10° C. After 6 hours in an ice bath then 16 hours at room temperature, the acetic and hydrochloric acids are distilled off under vacuum, without exceeding 50° C, then the excess phenol, without exceeding 85° C.

The crude product obtained is heated for an hour at boiling point under reflux with 250 ml of nitromethane. After cooling to 10° C and filtration, the product is dried at 50° C on a fluidised bed and 63 g of dried product are obtained (yield 60% with respect to the glyoxylic acid). This product has the following characteristics:

MP = 198° C
Acidimetry =
—COOH 4.74 m eq/g (theory 4.79)
—OH 4.68 m eq/g (theory 4.79)

| Elementary analysis | Calculated | Found |
|---|---|---|
| C | 57.45% | 57.3% |
| H | 5.25% | 5.3% |
| N | 6.70% | 6.7% |

The NMR in DMSO shows that the product obtained does not contain the orthohydroxyphenylglycine derivative. 20.9 g (0.1 mole) of the N-acetyl derivative are deacetylated by boiling for 3 hours in 133 ml of 3N hydrochloric acid, then 50 ml of water are distilled off; the resulting medium is cooled on ice and neutralised to pH 5.5 with concentrated ammonia. After cooling to 10° C, filtration, washing with water and acetone, then drying at 50° C, 16.3 g of crude product are obtained (yield 98%).

MP = 213°–215° C (with decomposition)

By recrystallisation of 12 g of this crude product in boiling water, one obtains 1st crop 8.5 g MP = 225°–228° C (with decomposition)
2nd crop 1.5 g MP = 220° C (with decomposition)

| | Acidimetry and Elementary Analysis: | | |
|---|---|---|---|
| | Calculated | Crude Product | 1st crop |
| —COOH | 5.99 m eq/g | 5.72 | 5.85 |
| —NH$_2$ | 5.99 m eq/g | 5.95 | 5.85 |
| G % | 57.5 | 56.8 | 57.4 |
| H % | 5.4 | 5.5 | 5.4 |
| N % | 8.4 | 8.7 | 8.4 |

EXAMPLE 8

N-chloracetyl (4-hydroxy phenyl) glycine 18 g of gaseous hydrochloric acid at 5° C are dissolved in a solution of 94 g (1 mole) of phenol and 83.8 g (0.5 mole) of chloracetamidoglycolic acid in 120 g of glacial acetic acid. After 8 hours at this temperature and then 16 hours at ambient temperature, the hydrochloric and acetic acids are distilled off at 25 mm of mercury, then the excess phenol at 2 mm of mercury at a temperature below 50° C, 200 ml of nitromethane are added, it is filtered, washed with ethyl ether and dried. 64 g of product are obtained (yield 53% with respect to the chloracetamidoglycolic acid). The product recrystallised in water melts at 187° C.

| Elementary Analysis | Calculated | Found |
|---|---|---|
| C | 49.28% | 49.32% |
| H | 4.10% | 4.10% |
| N | 5.74% | 5.67% |

EXAMPLE 9

N-Chloracetyl (4-hydroxy phenyl) glycine

Procedure is as in Example 8 up to and including the distillation of the phenol. The crude product obtained and suspended in 500 ml of water at 20° C is filtered, washed with water, then with ether and dried at 50° C under vacuum.

73.4 g of dry product are obtained (yield 60% with respect to the chloracetamidoglycolic acid).

The NMR spectrum of this product in DMSO shows that it does not contain the ortho hydroxyphenylglycine derivative.

The product recrystallised from water
MP = 187°–188° C (with decomposition)

| Elementary analysis | Calculated | Found |
|---|---|---|
| C | 49.28% | 49.3% |
| H | 4.1% | 4.1% |
| N | 5.74% | 5.7% |
| Cl | 14.4% | 14.5% |

By way of comparison, tests were carried out of the condensation of glyoxylic acid/aliphatic amide (carboxamidoglycolic acid) adduct products with phenol in an acetic acid — sulfuric acid medium, as is known to be done for the condensation of glyoxylic acid/aromatic amide adduct products with phenol. Unfortunately, the yields obtained were negligible on account of the difficulty of extracting the reaction product from the reaction medium due to the fact of its solubility in the latter.

Also, in order to carry out a more serious comparison, tests were carried out up to the stage of the free amino acid easier to isolate, by hydrolysing the N-acyl derivative by heating an acid medium.

EXAMPLE 10

Parahydroxyphenylglycine

To a solution in 120 g of acetic acid and 113.5 g of 95% sulfuric acid, of acetamidoglycolic acid obtained from 1 mole of glyoxylic acid, are added in 2 hours, 376 g (4 moles) of phenol in solution in 120 g of acetic acid, keeping the temperature below 5° C, then allowing to stand for 16 hours at room temperature. 1 liter of water is then added and it is boiled under reflux for 4 hours to hydrolyse the N-acyl derivative. After cooling to 20° C, the pH is brought to 1.5 with ammonia, the excess of phenol is extracted with 3 times 200 ml of butyl acetate. The aqueous phase concentrated at 1200 g is brought to pH 5.5 with ammonia, the precipitate formed is filtered, washed with water and dried.

Dry weight 54 g, namely a yield of 32% with respect to the glyoxylic acid.

MP = 221° C

EXAMPLE 11

Parahydroxyphenylglycine

To a solution in 120 g of acetic acid of acetamidoglycolic acid obtained from 0.5 mole of glyoxylic acid, 188 g (2 moles) of phenol are added, then by bubbling, 63 g of gaseous HCl therein at a temperature below 10° C. It is kept for 16 hours at ambient temperature, then 1 liter of water added and heated for 4 hours to boiling under reflux to hydrolyse the N-acetyl derivative. After cooling, it is brought to pH 1.5 with ammonia, then the phenol in excess is extracted with 3 times 200 ml of butyl acetate. The aqueous phase after concentration to 590 g is brought to pH 5.5 with ammonia. The precipitate formed is filtered, washed with water then dried.

Dry weight, 46 g, namely a yield of 54% with respect to the glyoxylic acid.

MP = 228° C.

In conclusion, it is observed that by using the process according to the invention, that is to say by effecting the condensation in the presence of hydrochloric acid instead of sulfuric acid, as is known to be done for glyoxylic acid/aromatic amide adduct products, one obtains a distinctly higher yield and a product of higher melting point, hence of greater purity.

We claim:

1. In a process of manufacturing N-acyl derivatives of hydroxyarylglycines by condensation of the adduct product of glyoxylic acid and amides with hydroxyaryl compounds having at least one free hydroxyl group and with at least one free position at the ortho or para position to the hydroxyl group, the improvement wherein said process comprises first reacting with heating at a temperature below about 60° C an aliphatic amide having at most 4 carbon atoms, with an aqueous solution of glyoxylic acid; then, after the addition of acetic acid and gaseous hydrochloric acid, condensing at low temperature below about 35° C the product resulting from the first step, which is the carboxamidoglycolic acid, with an excess of said hydroxyaryl compound; and isolating the resulting N-acyl hydroxyarylglycine derivative.

2. The improved process of claim 1, in which, after the first step, the carboxamidoglycolic acid is separated by crystallization.

3. The improved process of claim 1, in which an excess of the hydroxyaryl compound up to 500% is used.

4. The improved process according to claim 1, in which, after the second step, the volatile products are removed by vacuum distillation.

5. The improved process of claim 1, wherein, as aliphatic amide, use is made of amides having at the most 4 carbon atoms selected from the group consisting of acetamide, chloracetamide, propionamide, acrylamide and butyramide.

6. The improved process of claim 1, in which use is made, as the hydroxyaryl compound having at least one free hydroxyl group, of a compound selected from the group consisting essentially of: phenol, its alkyl derivatives and their halogen derivatives; polyphenols and their ethers and beta-naphthol.

7. The improved process of claim 1, wherein, after distillation of the volatile products from the medium resulting from the second step, the crude product is taken up again in a non-solvent of the N-acyl derivative of parahydroxyphenylglycine but solvent for the corresponding ortho derivative and its lactone, said non-solvent being selected from the group of nitromethane and water, whereby the proportion of the para derivative in the resulting product is of the order of 100%.

* * * * *